(12) United States Patent
Chiu et al.

(10) Patent No.: US 8,691,226 B2
(45) Date of Patent: Apr. 8, 2014

(54) HUMANIZED ANTI-HUMAN TUMOR NECROSIS FACTOR ALPHA MONOCLONAL ANTIBODY AND SEQUENCE THEREOF

(75) Inventors: Wei-Chun Chiu, Hsinchu County (TW); Min-Yuan Chou, Taipei (TW)

(73) Assignee: Industrial Technology Research Institute, Hsinchu (TW)

(*) Notice: Subject to any disclaimer, the term of this patent is extended or adjusted under 35 U.S.C. 154(b) by 610 days.

(21) Appl. No.: 12/979,125

(22) Filed: Dec. 27, 2010

(65) Prior Publication Data
US 2012/0100132 A1 Apr. 26, 2012

(30) Foreign Application Priority Data
Oct. 20, 2010 (TW) ................................ 99135701 A

(51) Int. Cl.
*A61K 39/395* (2006.01)
(52) U.S. Cl.
USPC .................................... 424/133.1; 530/387.1
(58) Field of Classification Search
None
See application file for complete search history.

(56) References Cited

U.S. PATENT DOCUMENTS

| | | | |
|---|---|---|---|
| 5,639,641 A | 6/1997 | Pendersen et al. | |
| 5,795,967 A | 8/1998 | Aggarwal et al. | |
| 6,448,380 B2 | 9/2002 | Rathjen et al. | |
| 7,402,662 B2 | 7/2008 | Athwal et al. | |
| 7,605,233 B2 | 10/2009 | Rathjen et al. | |
| 7,645,450 B2 | 1/2010 | Yoo et al. | |
| 7,744,885 B2 * | 6/2010 | Le et al. | 424/145.1 |
| 2007/0196373 A1 | 8/2007 | Le et al. | |

FOREIGN PATENT DOCUMENTS

| | | |
|---|---|---|
| CN | 1882611 | 12/2006 |
| CN | 101111521 | 1/2008 |
| CN | 101177453 | 5/2008 |
| JP | 2009131237 A | 6/2009 |
| WO | WO2009073533 | 6/2009 |

OTHER PUBLICATIONS

Chinese Office Action from corresponding Chinese application No. 201010539731.5, mailed on Apr. 7, 2013.
Fontayne et al., "Rational humanization of the powerful antithrombotic anti-GPIbα antibody:6B4," Thromb Haemost, 2006, pp. 671-684, vol. 96.
Zhang, "Humanization of an anti-human TNF-α anitbody by variable region resurfacing with the aid of molecular modeling," Molecular Immunology, 2005, pp. 1445-1451, vol. 42.
Staelens, "Humanization by variable domain resurfacing and grafting on a human IgG4, using a new approach for determination of non-human like surface accessible framework residues based on homology modelling of variable domains," Molecular Immunology, 2006, pp. 1243-1257, vol. 43.
Roguska, et al., "Humanization of murine monoclonal antibodies through variable domain resurfacing," Proc. Natl. Acad. Sci, USA, Feb. 1994, pp. 969-973, vol. 91.
Caron, "Human NK cells constitutively express membrane TNF-α (mTNFα) and present mTNFα-dependent cytotoxic activity," Eur. J. Immunol., 1999, pp. 3588-3595, vol. 29.
Arora, "Differences in binding and effector functions between classes of TNF antagonists," Cytokine, 2009, pp. 124-131, vol. 45.
Seneschal et al., "Cytokine imbalance with increased productions of interferon-α in psoriasiform eruptions associated with antitumour necrosis factor-α treatments," British Journal of Dermatology, 2009, pp. 1081-1088, vol. 161.
Scallon et al., "Chimeric anti-TNF-α monoclonal antibody cA2 binds recombanant transmembrane TNF-α and activates immune effector functions," Cytokine, Apr. 1995, pp. 251-259, vol. 7—No. 3.
Song et al., "Characterization of a novel anit-human TNF-α murine monoclonal antibody with high binding affinity and neutralizing activity," Experimental and Molecular Medicine, Feb. 2008, pp. 35-42, vol. 40—No. 1.
Padlan, Eduardo, "A possible procedure for reducing the immunogenecity of anitbody varaiable domains while preserving their ligand-binding properties," Molecular Immunology, 1991, pp. 489-498, vol. 28—No. 4/5.
Office Action mailed Sep. 24, 2012 in corresponding TW Application No. 099135701, pp. 1-8.
Office Action mailed Dec. 6, 2012 in corresponding JP Application No. 2010-291151, pp. 1-6, with English translation thereof.
Taylor, "Pharmacology of TNF blockade in rheumatoid arthritis and other chronic inflammatory diseases," Current Opinion in Pharmacology, Feb. 19, 2010, vol. 10, pp. 308-315.
Harrison et al., "Tumor Necrosis Factor α As a New Target for Renal Cell Carcinoma: Two Sequence Phase II Trials of Infliximab at Standard and High Dose," Journal of Clinical Oncology, Oct. 10, 2007, vol. 25, No. 29, pp. 4542-4549.
Knight et al., "Construction and Initial Characterization of a Mouse-Human Chimeric Anti-TNF Antibody," Molecular Immunology, vol. 30, No. 16, 1993, pp. 1443-1453.
Mitoma et al., "Mechanisms for Cytotoxic Effects on Anti-Tumor Necrosis Factor Agents on Transmembrane Tumor Necrosis Factor α-Expressing Cells," Arthritis & Rheumatism, vol. 58, No. 5, May 2008, pp. 1248-1257.

* cited by examiner

*Primary Examiner* — Laura B Goddard
*Assistant Examiner* — Meera Natarajan
(74) *Attorney, Agent, or Firm* — Muncy, Geissler, Olds & Lowe, P.C.

(57) ABSTRACT

An amino acid sequence of a humanized monoclonal antibody includes an amino acid sequence of a light chain variable region, which includes SEQ ID. NO.: 1; and an amino acid sequence of a heavy chain variable region, which comprises SEQ ID. NO.: 2, wherein SEQ ID. NO.: 1 and SEQ ID. NO.: 2 have at least one amino acid substitution which is selected from a group consisting of isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine.

11 Claims, 8 Drawing Sheets

HUMANIZED ANTI-HUMAN TUMOR NECROSIS FACTOR ALPHA MONOCLONAL ANTIBODY AND SEQUENCE THEREOF

CROSS REFERENCE TO RELATED APPLICATIONS

This Application claims priority of Taiwan Patent Application No. 099135701, filed on Oct. 20, 2010, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0965-A23521-US_Seq_Listing.txt"; its date of creation is Dec. 22, 2010; and its size is 9,320 bytes.

BACKGROUND OF THE INVENTION

1. Field of the Invention

The present disclosure relates to an anti-tumor necrosis factor-alpha antibody (TNF-α), and in particular relates to a humanized monoclonal antibody which is capable of highly neutralizing tumor necrosis factor-alpha, and an amino acid sequence thereof.

2. Description of the Related Art

Tumor necrosis factor-alpha (TNF-α) is a pro-inflammatory cytokine produced primarily by cells of the immune system, including macrophage and monocyte cells. TNF-α is present as a homotrimeric protein in which each subunit is initially translated as a 26 kDa transmembrane precursor protein. After being cleavaged at a site proximal to the transmembrane domain of TNF-α by the TNF-α converting enzyme (TACE), a soluble trimeric form of TNF-α is released and exerts its activity by binding to two structurally distinct type I and type II tumor necrosis factor receptors (TNFRI and TNFRII) on effector cells.

The transmembrane form of TNF-α is also known for its unique biologic functions, such as cytotoxic activity and polyclonal B cell activation, in a cell-to-cell contact manner (Mitoma et al., 2008). TNF-α has been proved to have a certain effect on autoimmune processes and has become a key therapy target for many autoimmune diseases (Feldmann, 2001). So far, some anti-TNF-α agents, like etanercept, adalimumab and infliximab have been approved by the Food and Drug Administration (FDA) of America, and all have the capability to neutralize the soluble form of TNF-α effectively as a major pharmacological mechanism of action. However, the binding effects of these antagonists on the transmembrane form of TNF-α are different, which may cause different results for clinical diseases (Taylor, 2010). For instance, etanercept is not clinically effective for the pathogenesis of granulomatous diseases, in which the transmembrane form of TNF-α may play a critical role (2008, Mitoma). Therefore, whether anti-TNF-α agents are capable of binding to the transmembrane form of TNF-α, is a prerequisite for triggering antibody dependent cell mediated cytotoxicity (ADCC), complement dependent cytotoxicity (CDC), apoptotic and outside-to-inside signaling mechanisms.

A major impediment for using the murine monoclonal antibody in clinical practice is that it may elicit human anti-murine antibody (HAMA) responses in patients (Owens and Young, 1994; Sandhu, 1992; Schroff et al., 1985). Hence, to improve efficiency in clinical use, genetic engineering technology has been employed to replace the murine content with the amino acid residues of human counterparts, which reduces the possibility of inducing immunogenicity in patients.

An ideal for antibody humanization is that it should be capable of maintaining specificity and affinity toward an antigen and reduce immunogenicity as much as possible. So far, many approaches have been used for antibody humanization, such as chimeric antibodies, which consists of murine antigen-binding variable regions fused genetically to human antibody constant regions, is the earliest attempt to reduce immunogenicity (Morrison et al., 1984). However, chimeric antibodies would still generate undesirable anti-variable region responses (Bruggemann et al., 1989). CDR-gtafting is another approach involving the transfer of the complementarity determining regions (CDRs) from a rodent antibody to the Fv frameworks (FRs) of a human antibody (Verhoeyen et al., 1988). Unfortunately, the interface changes between CDRs and new FRs may largely disturb the binding to the antigen. The initial CDR-grafted antibodies tend to lose parental binding affinity, and therefore require additional work for back-mutation of several murine framework amino acids, which are regarded to be crucial for CDR loop conformations (Queen et al., 1989). Humanization via variable domain resurfacing is another approach that can maintain the specificity and binding affinity of a parental antibody, which can reduce the immunogenicity of antibodies through the replacement of surface exposed residues in the murine FRs with those usually found in human antibodies (Fontayne et al., 2006; Padlan, 1991; Roguska et al., 1994; Staelens et al., 2006; Zhang et al., 2005). Although current molecular-biology techniques render this approach more straightforward in practice, determining the critical residues exposed in solvent on the surface of antibody is still difficult, especially when requiring a reliable computer model of the antibody (Fontayne et al., 2006).

BRIEF SUMMARY OF THE INVENTION

The disclosure provides an amino acid sequence of a humanized monoclonal antibody, comprising: an amino acid sequence of a light chain variable region, which comprises SEQ ID. NO.: 1; and an amino acid sequence of a heavy chain variable region, which comprises SEQ ID. NO.: 2, wherein SEQ ID. NO.: 1 and SEQ ID. NO.: 2 have at least one amino acid substitution, and the amino acid substitution is selected from a group consisting of isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine, and wherein the humanized monoclonal antibody is capable of binding to a tumor necrosis factor-alpha.

The disclosure provides another amino acid sequence of a humanized monoclonal antibody, comprising: an amino acid sequence of a light chain variable region, which comprises SEQ ID. NO.: 5; and an amino acid sequence of a heavy chain variable region, which comprises SEQ ID. NO.: 6, wherein the humanized monoclonal antibody is capable of binding to a tumor necrosis factor-alpha.

The disclosure also provides a nucleotide sequence of a humanized monoclonal antibody, comprising: a nucleotide sequence of a light chain variable region, which comprises SEQ ID. NO.: 7; and a nucleotide sequence of a heavy chain variable region, which comprises SEQ ID. NO.: 8, wherein the humanized monoclonal antibody is capable of binding to a tumor necrosis factor-alpha.

The disclosure further provides a humanized monoclonal antibody, comprising: a light chain, wherein an amino acid sequence of a variable region of the light chain comprises SEQ ID. NO.: 1; and a heavy chain, wherein an amino acid sequence of a variable region of the heavy chain comprises SEQ ID. NO.: 2, wherein SEQ ID. NO.: 1 and SEQ ID. NO.: 2 have at least one amino acid substitution, and the amino acid substitution is selected from a group consisting of isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine, and wherein the humanized monoclonal antibody is capable of binding to a tumor necrosis factor-alpha.

The disclosure further provides another humanized monoclonal antibody, comprising: a light chain, wherein an amino acid sequence of a variable region of the light chain comprises SEQ ID. NO.: 5; and a heavy chain, wherein an amino acid sequence of a variable region of the heavy chain comprises SEQ ID. NO.: 6, wherein the humanized monoclonal antibody is capable of binding to a tumor necrosis factor-alpha.

The disclosure further provides a method for neutralizing transmembrane tumor necrosis factor-alpha, comprising: providing a humanized monoclonal antibody to bind to a transmembrane tumor necrosis factor-alpha, wherein the humanized monoclonal antibody comprises: a light chain, wherein an amino acid sequence of a variable region of the light chain comprises SEQ ID. NO.: 5; and a heavy chain, wherein an amino acid sequence of a variable region of the heavy chain comprises SEQ ID. NO.: 6.

The disclosure further provides a method for inducing antibody-dependent cell-mediated cytotoxicity, comprising: providing a humanized monoclonal antibody to a subject to bind to a transmembrane tumor necrosis factor-alpha in the subject, wherein the humanized monoclonal antibody comprises: a light chain, wherein an amino acid sequence of a variable region of the light chain comprises SEQ ID. NO.: 5; and a heavy chain, wherein an amino acid sequence of a variable region of the heavy chain comprises SEQ ID. NO.: 6.

The disclosure further provides a method for preparing a drug for treating a transmembrane tumor necrosis factor-alpha related disease, comprising: providing a humanized monoclonal antibody, wherein the humanized monoclonal antibody comprises: a light chain, wherein an amino acid sequence of a variable region of the light chain comprises SEQ ID. NO.: 5; and a heavy chain, wherein an amino acid sequence of a variable region of the heavy chain comprises SEQ ID. NO.: 6, and wherein the humanized monoclonal antibody is capable of binding to a transmembrane tumor necrosis factor-alpha.

A detailed description is given in the following embodiments with reference to the accompanying drawings.

BRIEF DESCRIPTION OF THE DRAWINGS

The present disclosure can be more fully understood by reading the subsequent detailed description and examples with references made to the accompanying drawings, wherein.

DETAILED DESCRIPTION OF THE INVENTION

Figure 1:
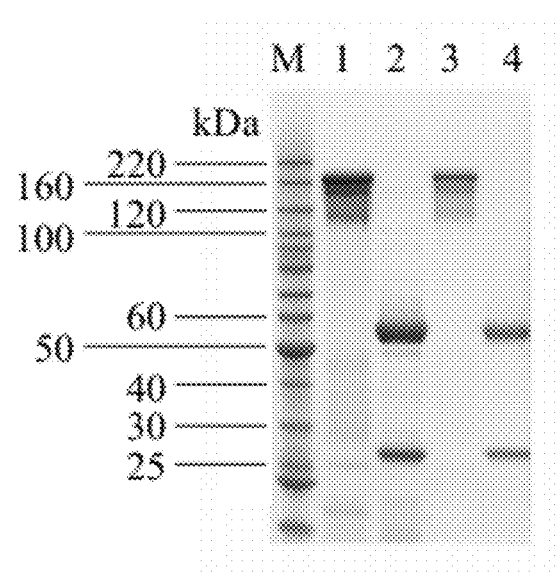
FIG. 1 shows SDS-PAGE analysis results for purified m357 IgG and h357 IgG. The m357 IgG (lane 1 and 2) and h357 IgG (lane 3 and lane 4) were expressed in mouse myeloma NS0 cells and purified from culture media by a protein A column. The samples were electrophoresed on a 4-12% SDS/Bis-Tris polyacrylamide gel with an MOPS buffer under non-reducing conditions (lanes 1 and 3) and reducing conditions (lanes 2 and 4). The gel was stained with Commassie blue. M, molecular mass standards.

The following description is of the best-contemplated mode of carrying out the invention. This description is made for the purpose of illustrating the general principles of the invention and should not be taken in a limiting sense. The scope of the invention is best determined by reference to the appended claims.

In one aspect of the invention, the disclosure provides an amino acid sequence of a humanized monoclonal antibody, wherein the humanized monoclonal antibody is capable of binding to a tumor necrosis factor-alpha (TNF-α), and the TNF-α may be a human TNF-α. The amino acid sequence of the humanized monoclonal antibody may comprise an amino acid sequence of a light chain variable region and an amino acid sequence of a heavy chain variable region. In one embodiment, the amino acid sequence of the humanized monoclonal antibody is an amino acid sequence of an immunoglobin G (IgG) antibody which may comprise an amino acid sequence of a light chain variable region, an amino acid sequence of a heavy chain variable region and an amino acid sequence of a constant region of a human immunoglobin G antibody.

In one embodiment, the amino acid sequence of the light chain variable region and the amino acid sequence of the heavy chain variable region of the invention may be obtained by performing variable domain resurfacing to a non-human monoclonal antibody which is capable of binding to a TNF-α.

First, an amino acid sequence of a light chain variable region and an amino acid sequence of a heavy chain variable region of a non-human monoclonal antibody which is capable of binding to a TNF-α, are obtained. In one embodiment, the non-human monoclonal antibody which is capable of binding to a TNF-α may comprise a murine monoclonal antibody. An amino acid sequence of a light chain variable region of the murine monoclonal antibody may comprise SEQ ID. NO.: 1, and an amino acid sequence of a heavy chain variable region of the murine monoclonal antibody may comprise SEQ D. NO.: 2.

Then, according to the amino acid sequence of the light chain variable region and the amino acid sequence of the heavy chain variable region of the non-human monoclonal antibody which is capable of binding to a TNF-α, a molecular model of the amino acid sequence of the light chain variable region and the amino acid sequence of the heavy chain variable region of the non-human monoclonal antibody is constructed, and non-constant surface residues thereof are labeled. In one embodiment, the molecular modeling process may be performed with computer-assisted homology modeling.

After that, a human sequence which has the highest sequence identity to the variable regions (light chain variable region and heavy chain variable region) of the non-human monoclonal antibody is searched for, and when found, a substitutable residue in the variable regions (light chain variable region and heavy chain variable region) of the non-human monoclonal antibody is determined following comparisons therebetween. Finally, the substitutable residue is substituted with the residue of the human sequence, which is located at a position corresponding to the position of the substitutable residue of the variable regions of the non-human monoclonal antibody, to obtain an amino acid sequence of a light chain variable region and an amino acid sequence of a heavy chain variable region of a humanized monoclonal antibody which is capable of binding to a TNF-α.

In one embodiment, the amino acid sequence of the light chain variable region of the non-human monoclonal antibody may comprise SEQ ID. NO.: 1 and the amino acid sequence of the heavy chain variable region of the non-human monoclonal antibody may comprise SEQ ID. NO.: 2 while the human sequence which has the highest sequence identity to the variable regions of the non-human monoclonal antibody may be the amino acid sequence of the light chain variable region of PPS4 (SEQ ID. NO.: 3) and the amino acid sequence of the heavy chain variable region of PPS4 (SEQ ID. NO.: 4). In the embodiment, the substitution which may be performed to the amino acid sequences of the light chain variable region and the heavy chain variable region of the non-human monoclonal antibody may at least comprise one of the following: isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine. Therefore, the obtained amino acid sequence of the humanized monoclonal antibody which is capable of binding to a TNF-α may comprise a light chain variable region amino acid sequence comprising SEQ ID. NO.: 1 and a heavy chain variable region amino acid sequence comprising SEQ ID. NO.: 2, wherein SEQ ID. NO.: 1 and SEQ. ID No: 2 have at least one amino acid substitution as follows: isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine.

In another embodiment, the amino acid sequence of the light chain variable region of the non-human monoclonal antibody may comprise SEQ ID. NO.: 1 and the amino acid sequence of the heavy chain variable region of the non-human monoclonal antibody may comprise SEQ ID. NO.: 2 while the human sequence which has the highest sequence identity to the variable regions of the non-human monoclonal antibody may be the amino acid sequence of the light chain variable region of PPS4 (SEQ ID. NO.: 3) and the amino acid sequence of the heavy chain variable region of PPS4 (SEQ ID. NO.: 4). After the sequence comparison mentioned above, the obtained amino acid sequence of the humanized monoclonal antibody which is capable of binding to a TNF-α may comprise a light chain variable region amino acid sequence comprising SEQ ID. NO.: 5 and a heavy chain variable region amino acid sequence comprising SEQ ID. NO.: 6.

Accordingly, in another aspect of the invention, the invention may also provide a nucleotide sequence of the humanized monoclonal antibody mentioned above. The nucleotide sequence of the humanized monoclonal antibody of the invention may comprise a nucleotide sequence of a light chain variable region and a nucleotide sequence of a heavy chain variable region. In one embodiment, the nucleotide sequence of the humanized monoclonal antibody is a nucleotide sequence of an immunoglobin G (IgG) antibody which may comprise a nucleotide sequence of a light chain variable region, a nucleotide sequence of a heavy chain variable region and a nucleotide sequence of a constant region of a human immunoglobin G antibody.

In one embodiment, the nucleotide sequence of a light chain variable region may comprise a nucleotide sequence encoding SEQ ID. NO.: 5, and the nucleotide sequence of a heavy chain variable region may comprise a nucleotide sequence encoding SEQ ID. NO.: 6. The nucleotide sequence encoding SEQ ID. NO.: 5 may be SEQ ID. NO.: 7, and the nucleotide sequence encoding SEQ ID. NO.: 6 may be SEQ ID. NO.: 8.

In another aspect of the invention, the invention further provides a humanized monoclonal antibody, wherein the humanized monoclonal antibody is capable of binding to a TNF-α, and the TNF-α may be a human TNF-α. The humanized monoclonal antibody may comprise a light chain and a heavy chain. In one embodiment, the humanized monoclonal antibody is an immunoglobin G (IgG) antibody, wherein a single chain thereof may comprise a light chain variable region, a heavy chain variable region and a constant region of a human immunoglobin G antibody.

In one embodiment, the humanized monoclonal antibody of the invention may be obtained by the following steps.

First, a nucleotide fragment of a light chain variable region and the sequence thereof and a nucleotide fragment of a heavy chain variable region and the sequence thereof of a non-human monoclonal antibody which is capable of binding to a TNF-α, is obtained. In one embodiment, the nucleotide fragments (cDNA) of the light chain variable region and the heavy chain variable region of the non-human monoclonal antibody may be obtained through extracting the total RNA of a hybridoma which is able to produce the non-human monoclonal antibody mentioned above, and performing a reverse-transcriptase polymerase chain reaction (RT-PCR) to the total RNA with two pairs of primers which correspond to the light chain variable region and the heavy chain variable region of the non-human monoclonal antibody, respectively. Then, the nucleotide fragments of the light chain variable region and the heavy chain variable region of the non-human monoclonal antibody are sequenced, respectively, to obtain the nucleotide sequences of the light chain variable region and the heavy chain variable region of the non-human monoclonal antibody, respectively. In one embodiment, the non-human monoclonal antibody which is capable of binding to a TNF-α may comprise a murine antibody. The nucleotide sequence of the light chain variable region of the murine antibody may comprise SEQ ID. NO.: 9, and the nucleotide sequence of the heavy chain variable region of the murine antibody may comprise SEQ ID. NO.: 10.

Next, the amino acid sequences of the light chain variable region and the heavy chain variable region of the non-human monoclonal antibody may be acquired, respectively, based on the nucleotide sequences of the light chain variable region and the heavy chain variable region of the non-human monoclonal antibody. In one embodiment, the amino acid sequences of the light chain variable region of the non-human monoclonal antibody may comprise a SEQ ID. NO.: 1 and the amino acid sequences of the heavy chain variable region of the non-human monoclonal antibody may comprise a SEQ ID. NO.: 2.

Afterward, according to the amino acid sequence of the light chain variable region and the amino acid sequence of the heavy chain variable region of the non-human monoclonal antibody which is capable of binding to a TNF-α, a molecular model of the amino acid sequence of the light chain variable region and the amino acid sequence of the heavy chain variable region of the non-human monoclonal antibody is constructed, and a non-constant surface residue thereof is labeled. In one embodiment, the molecular-modeling process may be performed with computer-assisted homology modeling.

Thereafter, a human sequence which has the highest sequence identity to the variable regions of the non-human monoclonal antibody is searched for, and when found, a substitutable residue in the variable regions (light chain variable region and heavy chain variable region) of the non-human monoclonal antibody is determined following comparisons therebetween. Finally, by point mutation, the nucleotides encoding the substitutable residue, of the nucleotide sequences of the variable regions of the non-human monoclonal antibody, is substituted with nucleotides encoding the residue of the human sequence, to obtain a nucleotide fragment of the light chain variable region and a nucleotide fragment of the heavy chain variable region of the human monoclonal antibody of the invention, wherein the residue of the human sequence is located at a position corresponding to the position of the substitutable residue of the variable regions of the non-human monoclonal antibody.

Then, the nucleotide fragment of the light chain variable regions and the nucleotide fragment of the heavy chain variable regions of the human monoclonal antibody capable of binding to a TNF-α of the invention and a nucleotide fragment of a known human antibody constant region are separately cloned into an appropriate expression vector, and the expression vector is transfected into an appropriate host cell so that the host cell expresses the human monoclonal antibody capable of binding to a TNF-α of the invention.

In one embodiment, the amino acid sequence of the light chain variable region of the non-human monoclonal antibody may comprise SEQ ID. NO.: 1 and the amino acid sequence of the heavy chain variable region of the non-human monoclonal antibody may comprise SEQ ID. NO.: 2 while the human sequence which has the highest sequence identity to the variable regions (light chain variable region and heavy chain variable region) of the non-human monoclonal antibody may be the amino acid sequence of the light chain variable region of PPS4 (SEQ ID. NO.: 3) and the amino acid sequence of the heavy chain variable region of PPS4 (SEQ ID. NO.: 4). In the embodiment, the substitution which may be performed to the amino acid sequences of the light chain variable region and the heavy chain variable region of the non-human monoclonal antibody may at least comprise one of the following: isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine. Therefore, the obtained amino acid sequence of the humanized monoclonal antibody which is capable of binding to a TNF-α may comprise a light chain variable region amino acid sequence comprising SEQ ID. NO.: 1 and a heavy chain variable region amino acid sequence comprising SEQ ID. NO.: 2, wherein SEQ ID. NO.: 1 and SEQ. ID No: 2 have at least one amino acid substitution as follows: isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine.

In another embodiment, the amino acid sequence of the light chain variable region of the non-human monoclonal antibody may comprise SEQ ID. NO.: 1 and the amino acid sequence of the heavy chain variable region of the non-human monoclonal antibody may comprise SEQ ID. NO.: 2 while the human sequence which has the highest sequence identity to the variable region (light chain variable region and heavy chain variable region) of the non-human monoclonal antibody may be the amino acid sequence of the light chain variable region of PPS4 (SEQ ID. NO.: 3) and the amino acid sequence of the heavy chain variable region of PPS4 (SEQ ID. NO.: 4). After the sequence comparison mentioned above, the obtained amino acid sequence of the humanized monoclonal antibody which is capable of binding to a TNF-α may comprise a light chain variable region amino acid sequence comprising SEQ ID. NO.: 5 and a heavy chain variable region amino acid sequence comprising SEQ ID. NO.: 6. Therefore, the humanized monoclonal antibody which is capable of binding to a TNF-α of the invention may comprise an amino sequence of a light chain variable region comprising SEQ ID. NO.: 5 and an amino sequence of a heavy chain variable region comprising SEQ ID. NO.: 6.

The TNF-α which is capable of binding to the humanized monoclonal antibody of the invention may comprise a released TNF-α or a transmembrane TNF-α. The binding affinity of the humanized monoclonal antibody to the released TNF-α may be about 20-40 nM, preferably about 10-20 nM.

Furthermore, the binding affinity of the humanized monoclonal antibody to the transmembrane TNF-α may be about 20-40 nM, preferably about 10-20 nM. In one embodiment, the binding affinity of the humanized monoclonal antibody of the invention to the transmembrane TNF-α may be about 16.8 nM.

In addition, in one embodiment, the humanized monoclonal antibody of the invention may induce antibody dependent cell mediated cytotoxicity (ADCC) by binding to a transmembrane TNF-α expressed on a cell.

At present, it is known that a transmembrane TNF-α is related to many diseases. For example, cell surface-expressed TNF-α like macrophages and monocytes play a very critical role in Granulomatous diseases such as Crohn's disease and Wegener's granulomatosis, and the cells can be killed directly by ADCC effect (Beenhouwer et al., 2004).

Accordingly, since the humanized monoclonal antibody of the invention is capable of binding to a transmembrane TNF-α and inducing an antibody dependent cell mediated cytotoxicity effect, in a further aspect of the invention, the invention may provide a method for neutralizing a transmembrane TNF-α and a method for inducing antibody-dependent cell-mediated cytotoxicity.

The method for neutralizing a transmembrane TNF-α may comprise providing a humanized monoclonal antibody of the invention to bind to a transmembrane TNF-α. Moreover, the method for inducing antibody-dependent cell-mediated cytotoxicity may comprise the step of providing a humanized monoclonal antibody of the invention to a subject to bind to a transmembrane TNF-α in the subject. In one embodiment, the subject may comprise a human.

In addition, the invention further provides a method for preparing a drug for treating a transmembrane TNF-α related disease. The method for preparing a drug for treating a transmembrane TNF-α related disease may comprise the step of providing a humanized monoclonal antibody, wherein the humanized monoclonal antibody is the humanized monoclonal antibody of the invention.

EXAMPLE

Material and Methods

A. Murine Antibody Capable of Binding to a Human TNF-α (TNF-α)

1. Obtainment and Purification of a Murine Antibody Capable of Binding to a Human TNF-α

A hybridoma cell line which is able to produce a murine antibody capable of binding to a human TNF-α 357-104-4 (ECACC No. 92030603) (purchased from European Collection of Cell Cultures) was injected into the abdominal cavity of a mouse so that the mouse produced tumor and ascites. The ascites produced by the mouse had a great quantity of murine antibody capable of binding to a human TNF-α (m357 IgG). GlycoNEX Inc. was commissioned to perform the steps mentioned above.

Then, the ascites was taken out from the mouse and purified by passing through a protein A column (GE Health-care) to obtain murine antibodies capable of binding to a human TNF-α (m357 IgG).

2. Obtainment of a cDNA Sequence of a Murine Antibody Capable of Binding to a Human TNF-α (m357 IgG)

(1) The total RNA of a hybridoma cell line 357-104-4 (ECACC No. 92030603) was extracted by using a QIAGEN RNeasy Mini Kit.

(2) A reverse-transcriptase polymerase chain reaction (RT-PCR) was performed to the total RNA with two primer pairs, Light Primer Mix and Heavy Primers manufactured by Amersham to obtain cDNA of a light chain of the m357 IgG and cDNA of a heavy chain of the m357 IgG, respectively.

(3) The cDNA of the light chain of the m357 IgG and the cDNA of the heavy chain of the m357 IgG were separately cloned into a TOPO vector to obtain two clones.

(4) After DNA sequencings were performed to the cDNA of the light chain of the m357 IgG and the cDNA of the heavy chain of the m357 IgG, respectively, two primer pairs corresponding to the cDNA of the light chain of the m357 IgG and the cDNA of the heavy chain of the m357 IgG, respectively, having enzyme restriction sites, were designed.

(5) The two primer pairs having enzyme restriction sites were synthesized.

The primer pair for the cDNA of light chain of the m357 IgG was:

```
357V_H5' Glink primer:
                                              (SEQ ID. NO.: 13)
5'-TCAGGCGGAGGTGGCTCTGGCGGTGGCGGATCGGTGAAACTGCAG

GA-3'

357V_H3'Not:
                                              (SEQ ID. NO.: 14)
5'-CAGCGGCCGCTGAGGAGACGGTGACCGTGGT-3'
```

The primer pair for the cDNA of heavy chain of the m357 IgG was:

```
357V_L' Asc primer:
                                              (SEQ ID. NO.: 11)
5'-CAGGCGCGCCGAAATTGTGCTGACCCAGTC-3'

357V_L3'Glink primer:
                                              (SEQ ID. NO.: 12)
5'-CCAGAGCCACCTCCGCCTGAACCGCCTCCACCCAATTTCCAGCTT

GC-3'
```

Then, polymerase chain reactions were performed to the two clones formed in step (3), respectively, to amplify the cDNA of the light chain of the m357 IgG and the cDNA of the heavy chain of the m357 IgG.

B. Computer Modeling of Murine Antibody Capable of Binding to a Human TNF-α (m357 IgG) for Resurfacing The homology modeling process of m357 IgG was performed using a Discovery Studio Modeling 2.1 (Accelrys, Inc., San Diego, Calif.). Two separate BLASTP searches were performed for the light chain variable region ($V_L$) and the heavy chain variable region ($V_H$) of m357. For identifying the homology of the m357 protein sequences, the sequences were analyzed by searching over the Protein Data Bank (PDB). A three-dimensional (3D) structure of the m357 IgG Fv fragment was constructed by homology modeling based on the structures of the $V_H$ domain of the murine anti-breast tumor antibody Fab fragment SM-3 [PDB entry: 1SM3] (Dokurno et al., 1998) and the $V_L$ domain structure of an anti-thermus aquaticus DNA polymerase I monoclonal antibody Fab fragment [PDB entry: 1AY1] (Murali et al., 1998). The final 3D model was generated by a MODELLER module (Sali et al., 1995), which implements an automated approach to comparative protein structure modeling by satisfaction of spatial restraints. Automatic protein homology modeling and loop modeling for m357 IgG were performed. Model building of the CDR loops were performed by selecting template structures from the PDB database with the highest sequence identity using the Model antibody Loops module and were refined using the Loop Refinement module in order to minimize steric clashes and ensure correct bond lengths and angles. Note that the model may be further refined by using a CHARMm (B. R. Brooks, 1983) with an Accelrys CHARMm forcefield in the Discovery Studio Modeling 2.1 for energy minimization. If so, the structure is energy-minimized in two steps. First, by 5000 steps of restrained steepest descent minimization, and next, by another 5000 steps of conjugated gradient minimization, while the alpha carbons of the framework are held in a fixed position. The solvent-accessible surface areas of the m357 IgG residues were calculated on the three-dimensional model by the AREAIMOL program (CCP4, 1994). The residues having relative accessibility greater than 30% were defined as being accessible.

C. Construction, Expression and Purification of IgG

The cDNA fragments encoding the humanized variable regions (light chain variable region and heavy chain variable region) of m357 IgG were obtained by overlapping PCR. The constant region sequences which came from human IgG and the variable region sequences which were synthesized by over-lapping PCR therewith, were sub-cloned into the mammalian expression vectors pSecTag2/Hygro (heavy chain) (Invitrogen) and pcDNA3.3-TOPO TA (light chain) (Invitrogen). The two constructs were then merged utilizing an EcoRV restriction site, yielding pSec-pcDNA-h357-IgG. Plasmids containing heavy and light chain genes were transfected into mouse myeloma NS0 cells (European Collection of Animal Cell cultures, Salisbury, Wiltshire, UK) using Effectene (Qiagen) according to manufacturer's instructions. After selection with Hygromycin (400 µg/ml) for 4 weeks, a stable clone was cultured in a shaker flask at an initial seeding density of $5 \times 10^5$ cells/ml in a serum free chemically-defined medium HyQNS0 (Hyclone). Media was harvested for 5 days at 37° C. and antibodies were purified from the supernatant by Protein A (GE Health-care) chromatography.

D. Anti-TNF-α Neutralization Potency Assay

Neutralizing activities of m357 IgG and h357 IgG against human TNF-α were measured on the murine fibroblast L929 cells (ATCC Cat. No. CCL-1) treated with actinomycin D according to the method described previously (Matthews N, 1987). Briefly, L929 cells were seeded in triplicate at $3 \times 10^5$ cells/well into a 96-well plate and cultured in a RPMI 1640 medium supplemented with 10% (v/v) of fetal bovine serum for 16 hours. Then, several dilutions of the antibodies were prepared in a medium containing actinomycin D (2 µg/ml) and TNF-α (100 ng/ml) and incubated at 37° C. for 16 hours. After the supernatants were removed, 3-4,5-dimethylthiazol-2-yl-2,5-diphenyltetrazolium bromide (MTT) (5 mg/ml) (Sigma-Aldrich) was added and incubated in 37° C. for 4 hours. An SDS solution (10%) was then added to the well. After 24 hours of incubation at room temperature, any change in color to purple in each well was recorded by a colorimeter. Optical density (OD) of the elution was determined at 570 nm, which had a positive correlation with number of survival cells. Blank control (culture alone), TNF-α control (TNF-α alone), and antibody control (antibody alone) were also designed in the experiment. The $ED_{50}$ value was calculated by a complex sigmoid non-linear regression analysis using Sigma plot software (Systat software, Inc. Richmond, Calif.).

E. Stable Expression of Transmembrane TNF-α on NS0 Cells

Deletion mutant transmembrane TNF-α resistant to TACE-mediated cleavage was generated by site-directed mutagenesis as described previously (Perez et al., 1990). In the uncleavable form of transmembrane TNF-α, the amino acids +1 through +12 of the native transmembrane TNF-α were deleted. An uncleavable form of transmembrane TNF-α gene was cloned into a pSecTag2/Hygro mammalian expression vector (Invitrogen) and transfected into mouse myeloma NS0 cells by Effectene for expressing transmembrane TNF-α on a cell surface.

F. Saturation Binding Assay of m357 IgG and h357 IgG to Transmembrane TNF-α

Transmembrane TNF-α transfected NS0 cells were incubated with serial log dilutions of m357 IgG and h357 IgG for 1 hour at 4° C. in phosphate buffered saline (PBS) containing 2% of a fetal bovine serum (fluorescence-activated cell sorting [FACS] buffer). Cells were washed with a FACS buffer 3 times and were then stained with an Alexa Fluor 488 goat anti-mouse IgG (H+L) for m357 IgG and an Alexa Fluor 647 goat anti-human IgG (H+L) for h357 IgG, respectively for 1 hour at 4° C. Fluorescence intensities were measured using a FACSCalibur flow cytometer (Becton Dickinson, San Jose, Calif.).

G. Antibody-Dependent Cell Mediated Cytotoxicity Assays

Antibody-dependent cell-mediated cytotoxicity (ADCC) activity of h357 IgG was measured by LDH Cytotoxicity Detection Kit (Clontech), which measures LDH activity released from the cytosol of damaged cells, according to manufacture's instructions. Briefly, the cells which can highly express transmembrane TNF-α were incubated in the presence of different concentrations of h357 antibodies for 1 hour in an assay medium (DMEM with 1% FBS) in a 5% $CO_2$ incubator at 37° C., and added human peripheral blood mononuclear cells (PBMC) as effector cells (effector to target, 20:1) thereafter. After additional incubation for 16 hours at 37° C., 100 µl of supernatant per well was harvested and transferred into a new 96-well, flat-bottom plate. An LDH substrate (100 µl) was added to each well and incubated for 30 min at room temperature (RT) while being protected from light. The absorbance of the samples was measured at 490 nm with an ELISA reader. Maximum release was determined by lysis buffer. Percentage of specific lysis was calculated according to the following formula: % cytotoxicity=[experimental release−spontaneous release]/[maximum release−spontaneous release]×100.

Results

A. Murine Antibody Capable of Binding to a Human TNF-α (m357 IgG)

1. Analysis of Murine Antibody Capable of Binding to a Human TNF-α

An SDS-PAGE analysis was performed to the purified m357 IgG and the results are shown as lane 1 and lane 2 of FIG. 1. Lane 1 shows a SDS-PAGE analysis result for purified m357 IgG at a non reducing condition; Lane 2 shows a SDS-PAGE analysis result for purified m357 IgG at a reducing condition.

Figure 2:
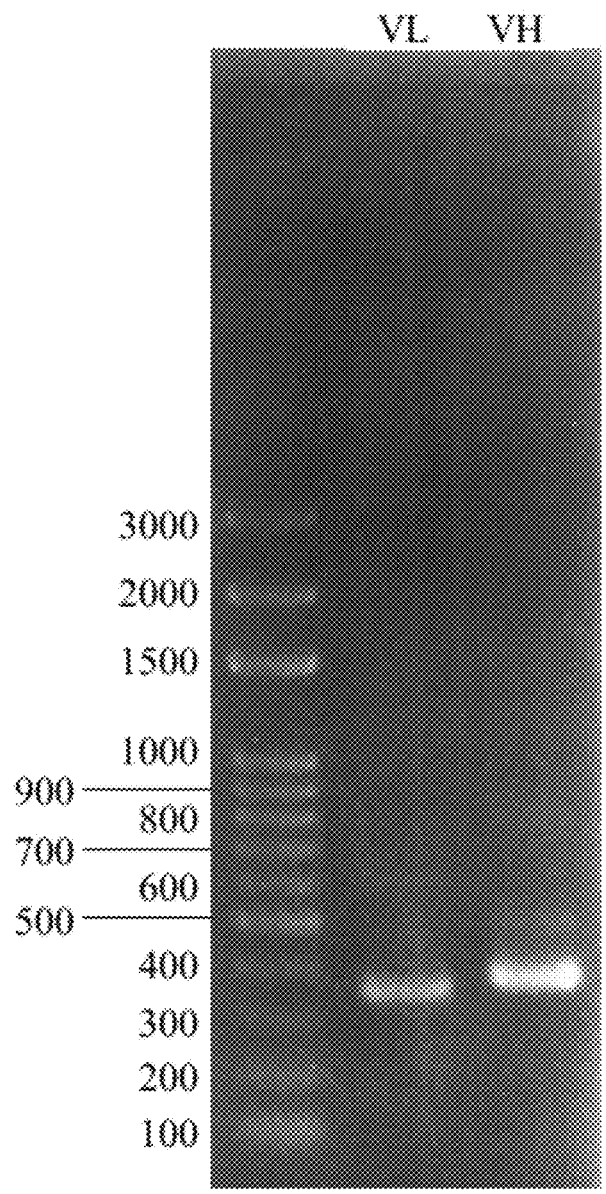
FIG. 2 shows electrophoresis results for the cDNA of the light chain of m357 IgG and the cDNA of the heavy chain of m357 IgG, respectively.

2. cDNA of the Light Chain of the m357 IgG and cDNA of the Heavy Chain of the m357 IgG The cDNA of the light chain of the m357 IgG and the cDNA of the heavy chain of the m357 IgG obtained by the polymerase chain reactions mentioned above were analyzed by an electrophoresis and the results are shown as FIG. 2, wherein lane 1 shows cDNA of the light chain of the m357

IgG (SEQ ID. NO.: 9) and lane 2 shows cDNA of the heavy chain of the m357 IgG (SEQ ID. NO.: 10).

B. Molecular Modeling of m357 IgG Variable Fragments

The cDNAs encoding the heavy chain variable region ($V_H$) and the light chain variable region ($V_L$) of an anti-TNF-α monoclonal antibody m357 IgG, derived from the hybridoma cell line, 357-101-4 (ECACC No. 92030603), were obtained by RT-PCR (data not shown). The three-dimensional structure of the deduced amino acid sequences of the $V_H$ and $V_L$ domains of m357 IgG was constructed individually by homology modeling (program MODELLER) as described under "Material and Methods." Afterward, the $V_H$ and $V_L$ domains of m357 IgG were modeled against the template structures 1SM3 (sharing 87% and 93% in sequence identity and similarity, respectively) at 1.95 Å resolution and 1AY1 (sharing 85% and 91% in sequence identity and similarity, respectively) at 2.20 Å resolution from PDB, respectively. The final refined structures of the $V_H$ and $V_L$ domains of m357 IgG were obtained through a Discovery Studio modeling 2.1 program as shown in FIG. 3A.

Figure 3A:
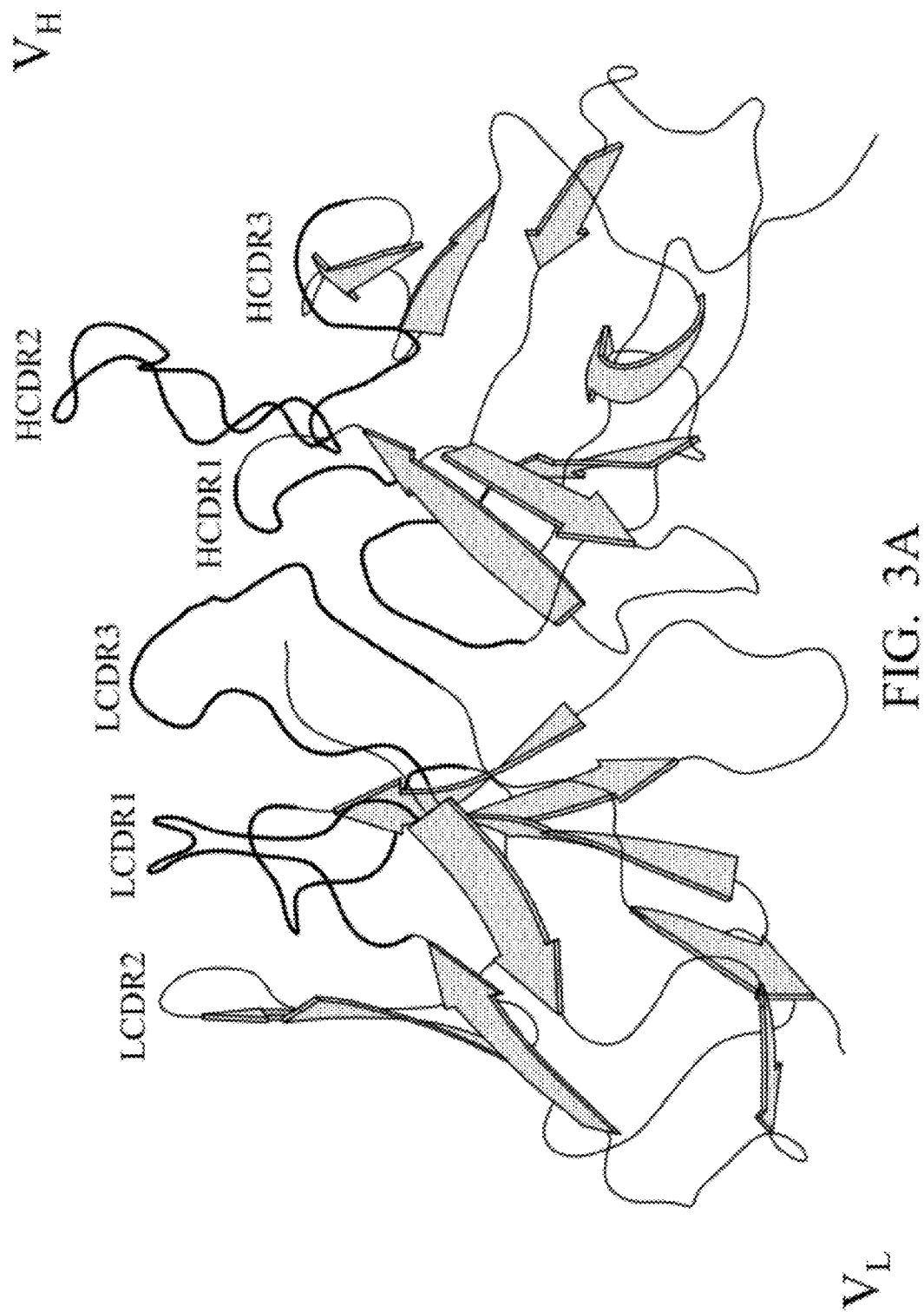
FIG. 3A shows the final refined structures of the $V_H$ and $V_L$ domains of m357 IgG.
Figure 3B:
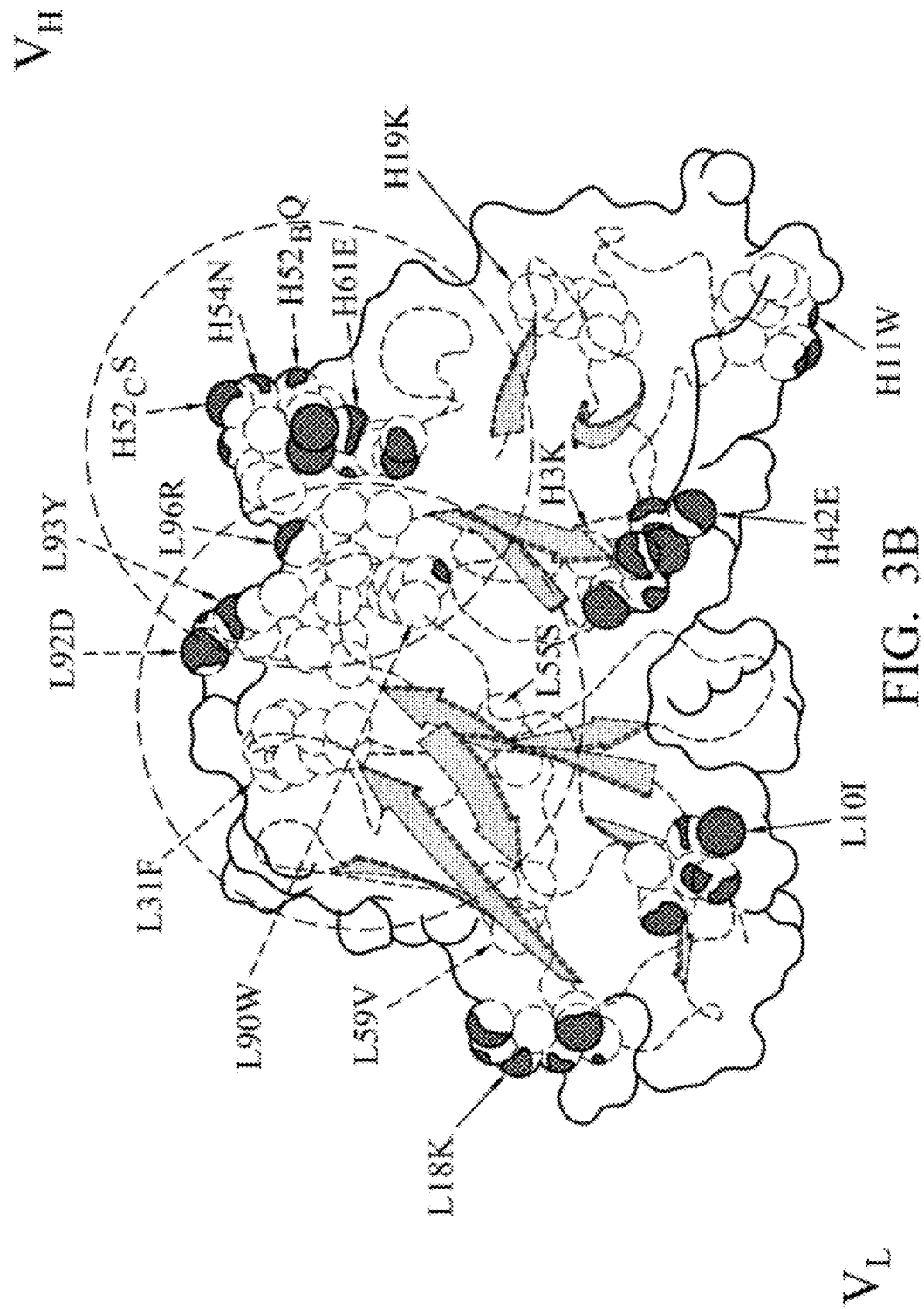
FIG. 3B shows the molecular surface model of m357 IgG.

FIG. 3A shows the variable region of the m357 IgG. The three-dimensional structure of m357 IgG was generated by homology modeling, by comparing the crystal structures of a 1SM3 for a $V_H$ domain and a 1 AY1 for a $V_L$ domain, respectively. The CDR loops are shown as a thick line. FIG. 3B shows the molecular surface model of m357 IgG, which shows that the non-human like surface residues are in relation to the CDR loops. The 17 residues, which were represented as blue spheres, and had relative solvent accessibility of more than 30%, are non-human like surface residues. The CDR loops are shown as a thick line. The residues near the CDR loops within 5 Å (the dashed circle) are labeled in pink text. The six residues which are preferably mutated to "human" amino acids are identified by arrow marks. Four residues in the $V_H$ framework were determined to be humanized whereas only two residues in the $V_L$ framework were determined to be humanized.

Humanization of m357 IgG Variable Fragments

Figure 4:
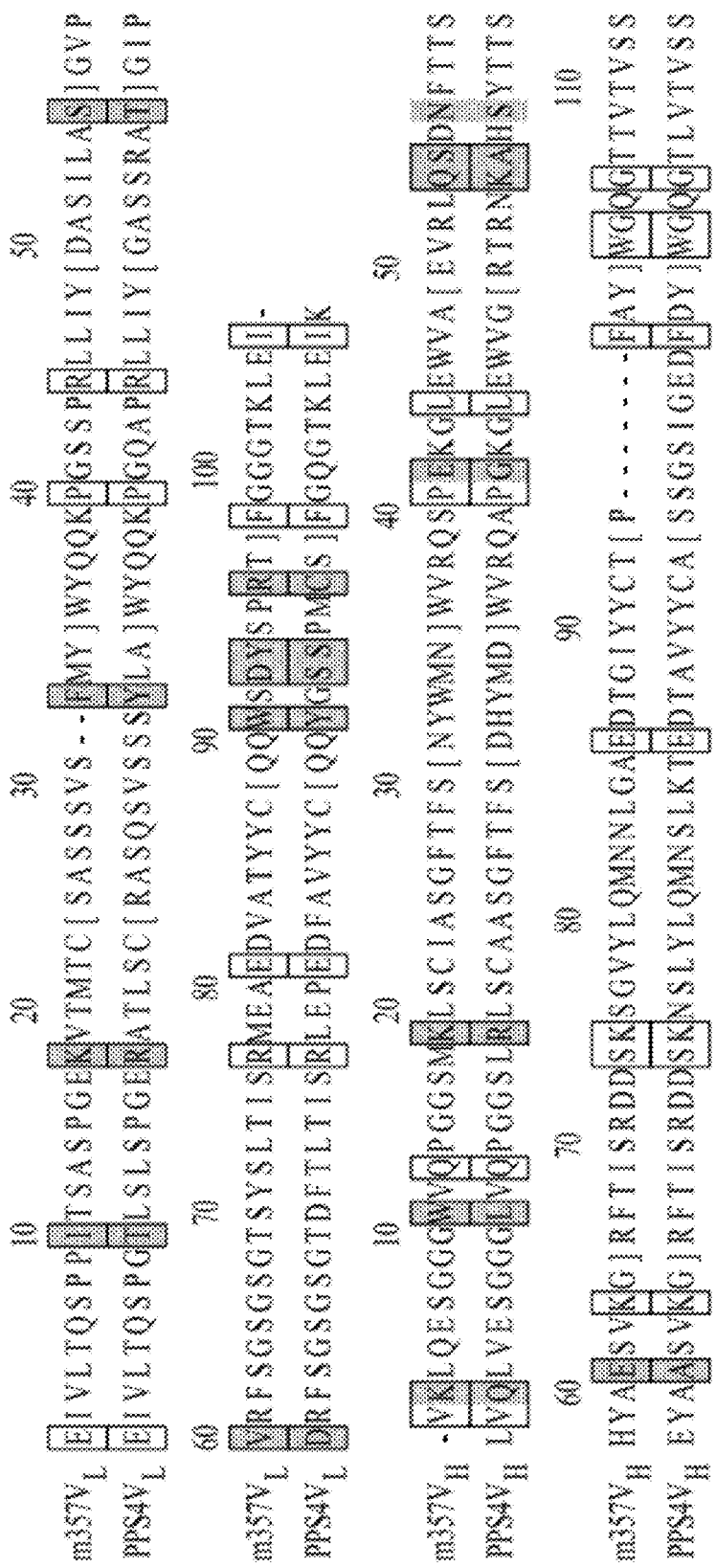
FIG. 4 shows amino acid sequence alignments of $V_H$ (A) and $V_L$ (B) domains of m357 IgG and PPS4. The sequences of PPS4 Fv which were the most homologous to m357 IgG Fv used as the acceptor of human surface residues for m357 IgG humanization is shown as PPS4$V_L$ and PPS4$V_H$ for comparison. CDR residues were within brackets ([ ]) Conserved surface residues were marked with clear boxes, and non-conserved surface residues were marker with shadowed boxes. Amino acid sequences are numbered according to the Kabat's convention (Kabat, 1991)
Figure 5:
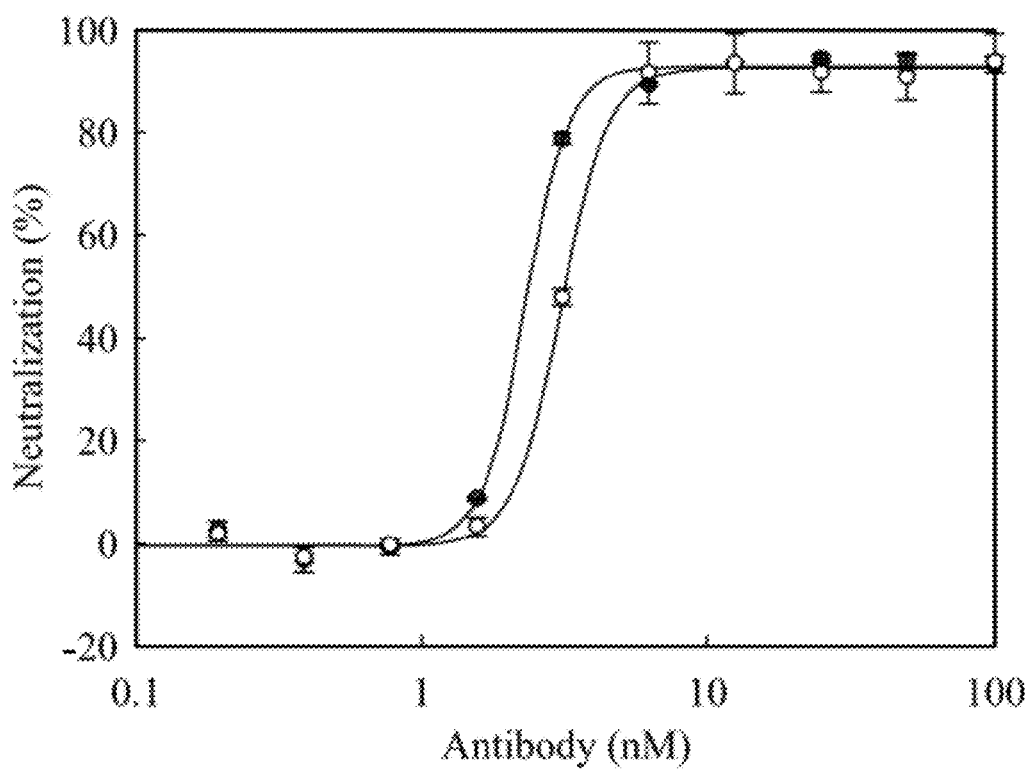
FIG. 5 shows the neutralization of tumor necrosis factor-alpha (TNF-α)-mediated cytotoxicity in L929 cells by m357-IgG and h357-IgG antibodies. Various concentrations of m357-IgG (●) and h357-IgG (○) antibodies were added to L929 cells cultured with 100 ng/ml of human TNF-α. The cells were incubated for 16 hrs at 37° C. and cell viability was analyzed using a colorimetric MTT assay.

Humanization by variable domain resurfacing was first proposed by Padlan in 1991, in which the potential antigenic sites in the framework regions of an antibody were eliminated without affecting the antigen binding affinity of the antibody (Padlan, 1991). This method is based on the hypothesis that the human anti-mouse antibody (HAMA) response of the variable region is derived only from the surface residues and has been adopted and modified by other researchers (Fontayne et al., 2006; O'Connor et al., 1998; Staelens et al., 2006). In the example, the variable domain resurfacing of m357 IgG was performed by the following three steps: first, the molecular models of the $V_H$ and $V_L$ domains of m357 IgG were constructed individually; second, the AREAIMOL program was used to calculate the solvent accessible residues for identifying the non-human like framework surface residues; and finally, the surface residues were mutated to the human counterparts according the results of the sequence alignment of human framework. In order to replace the non-human like framework surface residues of the murine m357 IgG on the variable domain, a set of highly homologous surface residues from a human target sequence were selected. A search was performed in the IMGT database (http://imgt.cines.fr/) to identify the human $V_H$ and $V_L$ sequence pairs, which are most homologous to corresponding variable regions of m357 IgG, while eliminating the sequences of phage-display or humanized antibodies from the search results. The most identical surface residues found from human sequences were the variable regions of PPS4 ($V_H$: 76% and $V_L$: 73% in the sequence identity in the framework regions, respectively) (FIG. 4).

According to the calculation results of the AREAIMOL program, 8 out of the 20 surface residues in the $V_H$ were non-conserved between human and mouse sequences and 9 out of 16 surface residues were non-conserved in the $V_L$. The 17 (8 plus 9) surface residues were determined to be the candidates for replacement. However, the substitution of H52BQ, H52CS, H54N, H61E, L31F, L55S, L90W, L92D, L93Y and L96R in CDR regions may potentially alter the CDR's conformation, and V59, an additional non-conserved surface residue in light chain near the CDR2 within 5 Å, may potentially affect the binding affinity (FIG. 3B). As a result, the 11 murine residues were retained for preserving antigen binding affinity. Finally, the remaining 6 residues shown in the following were chosen to be replaced with the human conserved residues: as compared with the light chain variable region of PPS4, isoleucine at comparative position 10 for the light chain variable region of m357 IgG, being substituted with threonine (isoleucine at position 10 of the light chain variable region of the m357 IgG, being substituted with threonine), lysine at comparative position 18 for the light chain variable region of the m357 IgG, being substituted with arginine (lysine at position 18 of the light chain variable region of the m357 IgG, being substituted with arginine); as compared with the heavy chain variable region of PPS4, lysine at comparative position 3 for the heavy chain variable region of the m357 IgG, being substituted with glutamine (lysine at position 2 of the heavy chain variable region of the m357 IgG, being substituted with glutamine), tryptophan at comparative position 11 for the heavy chain variable region of the m357 IgG, being substituted with leucine (tryptophan at position 10 of the heavy chain variable region of the m357 IgG, being substituted with leucine), lysine at comparative position 19 for the heavy chain variable region of the m357 IgG, being substituted with arginine (lysine at position 18 of the heavy chain variable region of the m357 IgG, being substituted with arginine) and glutamic acid at comparative position 42 for the heavy chain variable region of the m357 IgG, being substituted with glycine (glutamic acid at position 41 of the heavy chain variable region of the m357 IgG, being substituted with glycine).

D. Construction and Expression of the Humanized 357 (h357) $IgG_1$

The amino acid sequences of the humanized $V_H$ and $V_L$ of m357 were in-frame fused to the human $IgG_1$ heavy chain and kappa light chain constant regions, respectively. For the expression of an intact humanized 357 (h357) $IgG_1$ molecule, two different mammalian expression vectors, pSecTag2/Hygro and pcDNA3.3-TOPO TA, were used to adopt the humanized heavy chain and light chain of h357 IgG, respectively. Then, the light chain expression cassette was ligated to the pSecTag2/Hygro vector, resulting in a single-expression vector. The expression level of the recombinant h357 IgG was ~14 mg/L. The culture media containing m357 IgG and the culture media containing h357 IgG were purified by protein A chromatography, individually, and the protein purities were determined by the SDS-PAGE (FIG. 1). As shown in FIG. 1, under non-reducing conditions, both antibodies showed a single band with a molecular mass of 155 kDa (lanes 1 and 3). Under reducing conditions, both antibodies yielded two protein bands with molecular masses of 55 kDa (heavy chain) and 26 kDa (light chain) (lanes 2 and lane 4).

E. Neutralization of TNF-α-Mediated Cellular Cytotoxicity by m357 and h357

To examine the functional activity of the anti-TNF-α antibodies, the ability of the antibody to inhibit soluble TNF-α activity was performed. TNF-α causes cell cytotoxicity to murine L929 cells. Both m357 and h357 IgGs were evaluated in L929 assays by co-incubation of antibodies with recombinant human TNF-α and the cells. As shown in FIG. 4, TNF-α-mediated cytotoxicity in the L929 cells treated with 100 ng/ml of human TNF-α was effectively neutralized by both m357 and h357 IgGs in a dose dependent manner, with ED50 of 3.07 nM and 2.30 nM, respectively. The results indicated that the humanized 357 IgG retained TNF-α neutralization activity at concentrations similar to that of the murine 357 IgG.

F. Binding Activity of h357 to Transmembrane TNF-α

Figure 6:
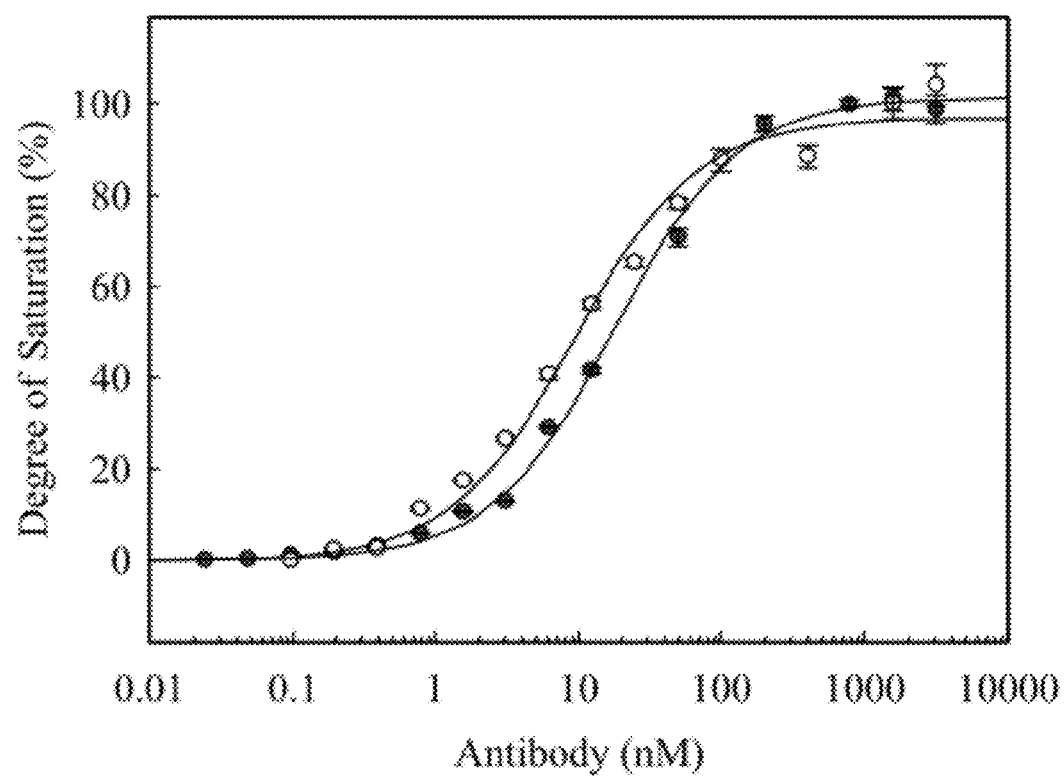
FIG. 6 shows the saturation binding assay of m35-IgG and h357-IgG antibodies to transmembrane TNF-α on a cell surface. Transmembrane TNF-α-transfected NS0 cells were incubated with serial log dilutions of m357-IgG (○) or h357-IgG (●) antibodies for 1 hr at 4° C. The cells were washed and incubated with Alexa Fluor 488 goat anti-mouse IgG (H+L) for m357-IgG and Alexa Fluor 647 goat anti-human IgG (H+L) for h357-IgG, respectively for 1 hr at 4° C. The cell were then washed and analyzed by a FACSCalibur flow cytometer.

TNF-α exists as a membrane associated precursor (transmembrane TNF-α) from which a mature soluble form is released by proteolytic cleavage mediated by the TNF-α converting enzyme (TACE). Many studies have investigated that TNF-α antagonists can cause cell lysis by apoptotic, antibody dependent cell mediated cytotoxicity (ADCC), complement dependent cytotoxicity (CDC) and outside-to-inside signaling mechanisms given that it has the binding ability to transmembrane TNF-α (Arora et al., 2009; Caron et al., 1999; Mitoma et al., 2008; Scallon et al., 1995). To analyze the transmembrane TNF-α binding ability of h357, an uncleavable form of the transmembrane TNF-α cDNA was transfected into NS0 cells to express it on the cell surface, and flow cytometry was used to assess the binding activities of both m357 and h357 IgGs. The data in FIG. 6 indicated that both m357 and h357 IgGs can bind to transmembrane TNF-α in a concentration-dependent manner with $K_D$=12.0 nM and 16.8 nM, respectively. Similar KD values indicated that the humanization process did not alter transmembrane TNF-α binding affinity. The binding affinity in the nanomolar range suggested h357 IgG could potentially trigger more effector functions or an apoptosis mechanism through the transmembrane TNF-α.

G. Ability of h357 to Mediate Antibody Dependent Cell Mediated Cytotoxicity (ADCC)

Figure 7:
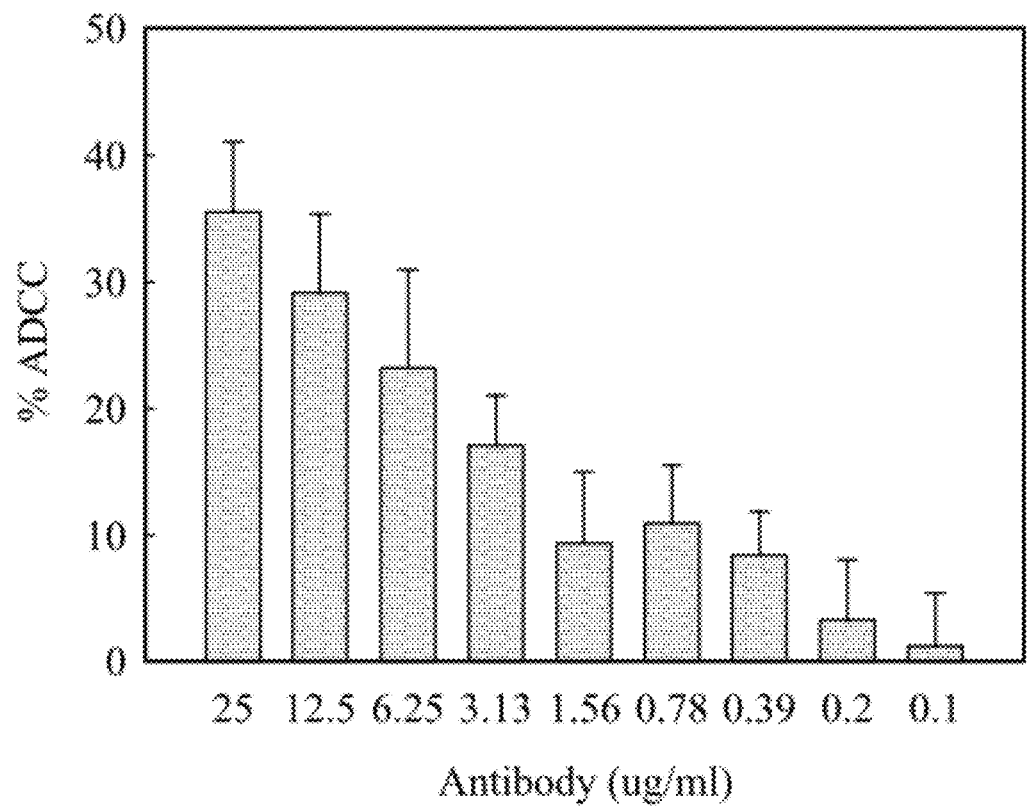
FIG. 7 shows the antibody-dependent cell mediated cytotoxicity of h357 IgG against transmembrane TNF-α-expressing cells. The transmembrane TNF-α-expressing cells were incubated in the presence of different concentrations of the h357 IgG antibody for 1 hour. Subsequently, PBMCs were used as effector cells and the transmembrane TNF-α-expressing cells were used as targets. The cytotoxicity was calculated by measuring the amount of LDH released from the cytosol into the supernatant. Results are presented as the percent of cell lysis compared to 100% lysis for the lysis buffer treated cell group.

Previous studies have been reported that the binding affinity of Infliximab and Adalimumab to the membrane form of TNF-α were better than that of Etanercept, which can affect the cell killing of cell surface-expressed transmembrane TNF-α by antibody dependent cell mediated cytotoxicity (ADCC), complement dependent cytotoxicity (CDC) or apoptosis mechanisms, and this may be one of the reasons that cause different effects on clinical diseases (Taylor, 2010). Cell surface-expressed TNF-α like macrophages and monocytes play a very critical role in the Granulomatous diseases such as Crohn's disease and Wegener's granulomatosis, and the cells can be killed directly by ADCC effect (Beenhouwer et al., 2004). When TNF-α antagonists bind to cells expressing the transmembrane form of TNF-α, these cells will be targeted by natural killer cells. h357 IgG consists of the Fc region derived from human $IgG_1$, which can potentially cause cell lysis in TNF-α-producing cells. Therefore, in order to assess the ability of h357 IgG to mediate ADCC against transmembrane TNF-α-expression target cells, the isolated PBMC were used in the ADCC assays at a 20:1 effector to target (E:T) ratio. More than 20% of the TNF-α bearing target cells were lysed by h357 IgG at 6.25 ug/ml (FIG. 7). The data indicates that h357 IgG can mediate ADCC effect upon binding to the transmembrane TNF-α expressed on the cell surface and therefore it has the potential to be developed into a more effective TNF-α-neutralizing antibody, which is similar to the therapeutic antibodies with ADCC capabilities.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A humanized monoclonal antibody, comprising: a light chain, wherein the amino acid sequence of a variable region of the light chain comprises SEQ ID. NO.: 1; and a heavy chain, wherein the amino acid sequence of a variable region of the heavy chain comprises SEQ ID. NO.: 2, wherein SEQ ID. NO.: 1 and SEQ ID. NO.: 2 have at least one amino acid substitution, and the amino acid substitution is selected from a group consisting of isoleucine at position 10 of SEQ ID. NO.: 1, being substituted with threonine, lysine at position 18 of SEQ ID. NO.: 1, being substituted with arginine, lysine at position 2 of SEQ ID. NO.: 2, being substituted with glutamine, tryptophan at position 10 of SEQ ID. NO.: 2, being substituted with leucine, lysine at position 18 of SEQ ID. NO.: 2, being substituted with arginine and glutamic acid at position 41 of SEQ ID. NO.: 2, being substituted with glycine, and wherein the humanized monoclonal antibody is capable of binding to a tumor necrosis factor-alpha.

2. The humanized monoclonal antibody as claimed in claim 1, wherein the tumor necrosis factor-alpha is a human tumor necrosis factor-alpha.

3. The humanized monoclonal antibody as claimed in claim 1, wherein the tumor necrosis factor-alpha comprises a released tumor necrosis factor-alpha or a transmembrane tumor necrosis factor-alpha.

4. The humanized monoclonal antibody as claimed in claim 3, wherein the binding affinity of the humanized monoclonal antibody to the transmembrane tumor necrosis factor-alpha is about 20-40 nM.

5. A humanized monoclonal antibody, comprising: a light chain, wherein the amino acid sequence of a variable region of the light chain comprises SEQ ID. NO.: 5; and a heavy chain, wherein the amino acid sequence of a variable region of the heavy chain comprises SEQ ID. NO.: 6, wherein the humanized monoclonal antibody is capable of binding to a tumor necrosis factor-alpha.

6. The humanized monoclonal antibody as claimed in claim 5, wherein the tumor necrosis factor-alpha is a human tumor necrosis factor-alpha.

7. The humanized monoclonal antibody as claimed in claim 5, wherein the tumor necrosis factor-alpha comprises a released tumor necrosis factor-alpha or a transmembrane tumor necrosis factor-alpha.

8. The humanized monoclonal antibody as claimed in claim 7, wherein the binding affinity of the humanized monoclonal antibody to the transmembrane tumor necrosis factor-alpha is about 20-40 nM.

9. A method for neutralizing transmembrane tumor necrosis factor-alpha, comprising: providing a humanized monoclonal antibody to bind to a transmembrane tumor necrosis factor-alpha, wherein the humanized monoclonal antibody comprises: a light chain, wherein the amino acid sequence of a variable region of the light chain comprises SEQ ID. NO.: 5; and a heavy chain, wherein the amino acid sequence of a variable region of the heavy chain comprises SEQ ID. NO.: 6.

10. A method for inducing antibody-dependent cell-mediated cytotoxicity, comprising: providing a humanized monoclonal antibody to a subject to bind to a transmembrane tumor necrosis factor-alpha in the subject, wherein the humanized monoclonal antibody comprises: a light chain, wherein the amino acid sequence of a variable region of the light chain comprises SEQ ID. NO.: 5; and a heavy chain, wherein the amino acid sequence of a variable region of the heavy chain comprises SEQ ID. NO.: 6.

11. A method for preparing a drug for treating a transmembrane tumor necrosis factor-alpha related disease, comprising: providing a humanized monoclonal antibody, wherein the humanized monoclonal antibody comprises: a light chain, wherein the amino acid sequence of a variable region of the light chain comprises SEQ ID. NO.: 5; and a heavy chain, wherein the amino acid sequence of a variable region of the heavy chain comprises SEQ ID. NO.: 6, and wherein the humanized monoclonal antibody is capable of binding to a transmembrane tumor necrosis factor-alpha.

\* \* \* \* \*

SEQUENCE LISTING

```
<160> NUMBER OF SEQ ID NOS: 14

<210> SEQ ID NO 1
<211> LENGTH: 107
<212> TYPE: PRT
<213> ORGANISM: Mus musculus

<400> SEQUENCE: 1

Glu Ile Val Leu Thr Gln Ser Pro Pro Ile Thr Ser Ala Ser Pro Gly
1               5                   10                  15

Glu Lys Val Thr Met Thr Cys Ser Ala Ser Ser Ser Val Ser Phe Met
            20                  25                  30

Tyr Trp Tyr Gln Gln Lys Pro Gly Ser Ser Pro Arg Leu Leu Ile Tyr
        35                  40                  45

Asp Ala Ser Ile Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Trp Ser Asp Tyr Ser Pro Arg
                85                  90                  95

Thr Phe Gly Gly Gly Thr Lys Leu Glu Ile Lys
            100                 105

<210> SEQ ID NO 2
```

-continued

```
<211> LENGTH: 113
<212> TYPE: PRT
<213> ORGANISM: Mus musculus

<400> SEQUENCE: 2

Val Lys Leu Gln Glu Ser Gly Gly Gly Trp Val Gln Pro Gly Gly Ser
1               5                   10                  15

Met Lys Leu Ser Cys Ile Ala Ser Gly Phe Thr Phe Ser Asn Tyr Trp
            20                  25                  30

Met Asn Trp Val Arg Gln Ser Pro Glu Lys Gly Leu Glu Trp Val Ala
        35                  40                  45

Glu Val Arg Leu Gln Ser Asp Asn Phe Thr Thr His Tyr Ala Glu Ser
    50                  55                  60

Val Lys Gly Arg Phe Thr Ile Ser Arg Asp Asp Ser Lys Ser Gly Val
65                  70                  75                  80

Tyr Leu Gln Met Asn Asn Leu Gly Ala Glu Asp Thr Gly Ile Tyr Tyr
                85                  90                  95

Cys Thr Pro Phe Ala Tyr Trp Gly Gln Gly Thr Val Thr Val Ser
            100                 105                 110

Ser

<210> SEQ ID NO 3
<211> LENGTH: 109
<212> TYPE: PRT
<213> ORGANISM: Homo sapiens

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Cys Ser Phe Gly Gln Gly Thr Lys Leu Glu Ile Lys
            100                 105

<210> SEQ ID NO 4
<211> LENGTH: 122
<212> TYPE: PRT
<213> ORGANISM: Homo sapiens

<400> SEQUENCE: 4

Leu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala His Ser Tyr Thr Thr Ser Glu Tyr Ala
    50                  55                  60

Ala Ser Val Lys Gly Arg Phe Thr Ile Ser Arg Asp Asp Ser Lys Asn
65                  70                  75                  80
```

Ser Leu Tyr Leu Gln Met Asn Ser Leu Lys Thr Glu Asp Thr Ala Val
            85                  90                  95

Tyr Tyr Cys Ala Ser Gly Ser Ile Gly Glu Asp Phe Asp Tyr Trp
            100                 105                 110

Gly Gln Gly Thr Leu Val Thr Val Ser Ser
            115                 120

<210> SEQ ID NO 5
<211> LENGTH: 107
<212> TYPE: PRT
<213> ORGANISM: Artificial
<220> FEATURE:
<223> OTHER INFORMATION: Humanized light chain variable region

<400> SEQUENCE: 5

Glu Ile Val Leu Thr Gln Ser Pro Pro Thr Thr Ser Ala Ser Pro Gly
1               5                   10                  15

Glu Arg Val Thr Met Thr Cys Ser Ala Ser Ser Val Ser Phe Met
            20                  25                  30

Tyr Trp Tyr Gln Gln Lys Pro Gly Ser Ser Pro Arg Leu Leu Ile Tyr
            35                  40                  45

Asp Ala Ser Ile Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Trp Ser Asp Tyr Ser Pro Arg
                85                  90                  95

Thr Phe Gly Gly Gly Thr Lys Leu Glu Ile Lys
            100                 105

<210> SEQ ID NO 6
<211> LENGTH: 113
<212> TYPE: PRT
<213> ORGANISM: Artificial
<220> FEATURE:
<223> OTHER INFORMATION: Humanized heavy chain variable region

<400> SEQUENCE: 6

Val Gln Leu Gln Glu Ser Gly Gly Leu Val Gln Pro Gly Gly Ser
1               5                   10                  15

Met Arg Leu Ser Cys Ile Ala Ser Gly Phe Thr Phe Ser Asn Tyr Trp
            20                  25                  30

Met Asn Trp Val Arg Gln Ser Pro Gly Lys Gly Leu Glu Trp Val Ala
            35                  40                  45

Glu Val Arg Leu Gln Ser Asp Asn Phe Thr Thr His Tyr Ala Glu Ser
        50                  55                  60

Val Lys Gly Arg Phe Thr Ile Ser Arg Asp Asp Ser Lys Ser Gly Val
65                  70                  75                  80

Tyr Leu Gln Met Asn Asn Leu Gly Ala Glu Asp Thr Gly Ile Tyr Tyr
                85                  90                  95

Cys Thr Pro Phe Ala Tyr Trp Gly Gln Gly Thr Thr Val Thr Val Ser
            100                 105                 110

Ser

<210> SEQ ID NO 7
<211> LENGTH: 321
<212> TYPE: DNA
<213> ORGANISM: Artificial
<220> FEATURE:

<223> OTHER INFORMATION: DNA of humanized light chain variable region

<400> SEQUENCE: 7

```
gaaattgtgc tgacccagtc tccaccaacc acgtctgctt ctccagggga gagagtcacc      60
atgacctgca gtgccagctc aagtgtaagt tcatgtact ggtaccagca gaagccagga     120
tcctccccca gactcctgat ttatgacgca tccatcctgg cttctggagt ccctgttcgc    180
ttcagtggca gtgggtctgg gacctcttac tctctcacaa tcagccgaat ggaggctgaa    240
gatgttgcca cttattactg ccaacaatgg agtgattact cacccaggac gttcggtgga    300
ggcaccaagc tggaaattaa a                                               321
```

<210> SEQ ID NO 8
<211> LENGTH: 340
<212> TYPE: DNA
<213> ORGANISM: Artificial
<220> FEATURE:
<223> OTHER INFORMATION: DNA of humanized heavy chain variable region

<400> SEQUENCE: 8

```
gtgcagctgc aggagtctgg aggaggcttg gtgcaacctg gaggatccat gagactctcc      60
tgtattgcct ctggattcac tttcagtaac tactggatga ctgggtccg ccagtctcca     120
gggaaggggc ttgagtgggt tgctgaagtt agattgcaat ctgataattt tacaacacat    180
tatgcggagt ctgtgaaagg gaggttcacc atctcaagag atgattccaa agtggtgtc    240
tacctgcaaa tgaacaactt aggagctgaa gacactggca tttattattg taccccgttt    300
gcttattggg gccaagggac cacggtcacc gtctcctcag                           340
```

<210> SEQ ID NO 9
<211> LENGTH: 321
<212> TYPE: DNA
<213> ORGANISM: Mus musculus

<400> SEQUENCE: 9

```
gaaattgtgc tgacccagtc tccaccaatt acgtctgctt ctccagggga gaaggtcacc      60
atgacctgca gtgccagctc aagtgtaagt tcatgtact ggtaccagca gaagccagga     120
tcctccccca gactcctgat ttatgacgca tccatcctgg cttctggagt ccctgttcgc    180
ttcagtggca gtgggtctgg gacctcttac tctctcacaa tcagccgaat ggaggctgaa    240
gatgttgcca cttattactg ccaacaatgg agtgattact cacccaggac gttcggtgga    300
ggcaccaagc tggaaattaa a                                               321
```

<210> SEQ ID NO 10
<211> LENGTH: 340
<212> TYPE: DNA
<213> ORGANISM: Mus musculus

<400> SEQUENCE: 10

```
gtgaaactgc aggagtctgg aggaggctgg gtgcaacctg gaggatccat gaaactctcc      60
tgtattgcct ctggattcac tttcagtaac tactggatga ctgggtccg ccagtctcca     120
gagaaggggc ttgagtgggt tgctgaagtt agattgcaat ctgataattt tacaacacat    180
tatgcggagt ctgtgaaagg gaggttcacc atctcaagag atgattccaa agtggtgtc    240
tacctgcaaa tgaacaactt aggagctgaa gacactggca tttattattg taccccgttt    300
gcttattggg gccaagggac cacggtcacc gtctcctcag                           340
```

<210> SEQ ID NO 11

```
<211> LENGTH: 30
<212> TYPE: DNA
<213> ORGANISM: Artificial
<220> FEATURE:
<223> OTHER INFORMATION: Artificial primer

<400> SEQUENCE: 11
caggcgcgcc gaaattgtgc tgacccagtc                                      30

<210> SEQ ID NO 12
<211> LENGTH: 47
<212> TYPE: DNA
<213> ORGANISM: Artificial
<220> FEATURE:
<223> OTHER INFORMATION: Artificial primer

<400> SEQUENCE: 12
ccagagccac ctccgcctga accgcctcca cccaatttcc agcttgc                   47

<210> SEQ ID NO 13
<211> LENGTH: 47
<212> TYPE: DNA
<213> ORGANISM: Artificial
<220> FEATURE:
<223> OTHER INFORMATION: Artificial primer

<400> SEQUENCE: 13
tcaggcggag gtggctctgg cggtggcgga tcggtgaaac tgcagga                   47

<210> SEQ ID NO 14
<211> LENGTH: 31
<212> TYPE: DNA
<213> ORGANISM: Artificial
<220> FEATURE:
<223> OTHER INFORMATION: Artificial primer

<400> SEQUENCE: 14
cagcggccgc tgaggagacg gtgaccgtgg t                                    31
```